United States Patent [19]

Lorenz et al.

[11] Patent Number: 4,704,453

[45] Date of Patent: Nov. 3, 1987

[54] PREPARATION OF ALKYLGLUCOSIDES

[75] Inventors: Klaus Lorenz, Worms; Wolf-Dieter Balzer, Ludwigshafen; Helmut Wolf, Hassloch; Wolfgang Trieselt, Ludwigshafen; Gerd Busse, Mutterstadt, all of Fed. Rep. of Germany

[73] Assignee: Basf Aktiengesellschaft, Ludwigshafen, Fed. Rep. of Germany

[21] Appl. No.: 528,794

[22] Filed: Sep. 2, 1983

[30] Foreign Application Priority Data

Sep. 3, 1982 [DE] Fed. Rep. of Germany ....... 3232791

[51] Int. Cl.$^4$ .............................................. C07G 3/00
[52] U.S. Cl. .................................. 536/18.6; 536/4.1; 536/124
[58] Field of Search .............. 536/123, 124, 127, 18.6, 536/4.1

[56] References Cited

U.S. PATENT DOCUMENTS 3,547,828 12/1970 Mansfield et al. .
4,298,728 11/1981 Majewicz .

Primary Examiner—Alan Siegel
Attorney, Agent, or Firm—Oblon, Fisher, Spivak, McClelland & Maier

[57] ABSTRACT

Alkylglucosides are prepared by acetalization of glucose with an equivalent amount or an excess of a $C_3$–$C_5$-alkanol in the presence of an acidic catalyst by a method wherein the acetalization is carried out in the presence of an alkali metal salt of a boric acid used in an amount which is equivalent to or in excess of the amount of the catalyst.

The alkylglucosides obtained can be used directly, for example as solubilizers, in particular in the cosmetic sector, or can be reacted further to give higher alkylglucosides.

3 Claims, No Drawings

PREPARATION OF ALKYLGLUCOSIDES

Lower alkylglucosides, especially n- or isobutylglucoside, are important intermediates for the preparation of higher alkylglucosides, whose use as alkali-stable surfactants is known. Furthermore, the hydrophilic and hydrophobic moieties in the molecule give the lower alkylglucosides the typical properties of solubilizers for hydrophobic substances.

The term lower alkylglucosides includes mixtures of alkylmonoglucosides and alkyloligoglucosides, the oligoglucosides containing as a rule from 2 to 10 glucose units. The fact that such mixtures are formed in the conventional acetalization of glucose in the presence of an acid catalyst is known to one skilled in the art.

The prior methods for their preparation generally comprised the acetalization of glucose with a $C_3$–$C_5$-alkanol, in general butanol, in the presence of an acid catalyst. German Laid-open Application DOS 1,943,689 discloses a two-stage process for the preparation of laurylglucoside in which, in the first stage, glucose is acetalized with butanol in the presence of a strong acid, e.g. sulfuric acid or p-toluene sulfnnic acid, and the butyl glucosides, or more exactly a mixture of butylmonoglucoside and butyloligoglucosides, are formed as intermediates in the reaction solution, from which they can be isolated or in which they can be transacetalized directly to higher alkylglucosides.

The disadvantage of this method is that the acetalization of the glucosides (which in general takes place at the boiling point of the butanol and with the resulting water of reaction being separated off) gives rise to dark by-products which have to be removed in a separate subsequent operation, for example by bleaching. It is known that these by-products are formed whenever carbohydrates are treated with acids, resulting from the elmination of water in a competing reaction.

It is an object of the present invention to provide a process which gives very by-product-free, pale $C_3$–$C_5$-alkylglucosides which can be readily isolated or processed further directly to higher alkylglucosides.

We have found that this object is achieved, surprisingly, by a process as defined in the claims.

In this process, an alkali metal salt of a boric acid is added to the reaction solution before or during the reaction, the amount of the salt added being equivalent to or in excess of the amount of the acidic catalyst. As a result, the catalytic acid is converted to its alkali metal salt, and the liberated boric acid is converted to a glucose/boric acid complex which, is a complex Lewis acid, in turn assumes the role of the acidic catalyst, giving substantially paler products. This finding is surprising in that it had been expected hitherto that acetalization of glucose would take place only in the presence of $H^{\oplus}$ ions in concentrations corresponding to a pH<3.

Advantageously, the alkali metal salt of a boric acid is added after the glucose has dissolved in the mixture of the alcohol used and the acidic catalyst.

The pale products can be readily converted to higher alkylglucosides by further transacetalization.

We have found that alkylglucosides which were prepared without the addition of the boron compounds and were treated with a bleaching agent, e.g. hydrogen peroxide or sodium perborate, only after the water of reaction had been removed were substantially darker in color than the products obtained in accordance with the invention.

The process is simple to carry out, the procedure being, for example, as follows: a $C_3$–$C_5$-alkanol, in particular a propanol, an amyl alcohol or mixtures of the alcohols conforming to the above definition, preferably isobutanol or n-butanol, is first mixed with glucose and the acidic catalyst, and the mixture is refluxed until a clear solution has formed. This takes in general about 15–45 minutes.

The alcohol can be present in an equivalent amount with respect to the glucose, but is more advantageously employed in excess, because the glucose is more readily soluble. It is particularly advantageous to use from 1.5 to 5 parts of alcohol per part of glucose. The glucose is advantageously employed in the anhydrous form.

The acidic catalysts employed for the above purpose are the conventionally used acids, e.g. sulfuric acid, phosphoric acid, hydrochloric acid or p-toluenesulfonic acid, preferably the last-mentioned acid. The reaction mixture contains the acidic catalyst in an amount of about 0.2–5, preferably 0.5–3, % by weight, based on glucose.

When this reaction mixture has cooled, preferably to about 80°–110° C., the alkali metal salt of a boric acid is added in an amount which is not less than that required to neutralize the acidic catalyst completely, i.e. an equivalent amount. Depending on the amount of acidic catalyst present, this amount is from 0.5 to 5 % by weight, based on glucose.

For the purposes of the present invention, alkali metal salts of a boric acid are, for example, borates of potassium or sodium, which are advantageously employed in the form of their hydrates. Sodium metaborate tetrahydrate and disodium tetraborate decahydrate (borax) are preferably used. Particularly advantageous results are obtained with those borates which contain hydrogen peroxide in bonded form (peroxohydrated borates), since the hydrogen peroxide liberated during the reaction has an additional bleaching effect, which, as stated above, cannot be achieved satisfactorily with this compound when it is employed after the reaction or separately during the reaction.

A preferably employed peroxohydrated borate is the compound sodium perborate. After the borates have been added, the procedure is carried out in a conventional manner as follows: the water is separated off by distillation, preferably in the presence of about 3–5 % by weight, based on the total mixture, of xylene as an entraining agent, the excess alkanol is distilled off, the mixture is, if required, neutralized, and the resulting glucoside is isolated or is directly processed further.

Particularly when they are prepared in the presence of peroxohydrated borates, the glucosides are obtained as virtually colorless products, and can therefore be used directly or reacted further with higher alcohols to give higher alkylglucosides. The glucosides, in particular n-butylglucoside, can be used as solubilizers and, because of their purity, are especially suitable for the cosmetic sector; furthermore, they are excellent starting materials for the preparation of higher alkylglucosides, which can likewise be obtained in a substantially paler state by any conventional method.

The Examples which follow illustrate the invention. Parts are by weight.

EXAMPLE 1

810 parts of n-butanol, 568 parts of anhydrous glucose and 9 parts of p-toluenesulfonic acid were refluxed for half an hour, the glucose going into solution. Thereafter, the mixture was cooled to 100° C. and 7.4 parts of sodium perborate tetrahydrate were added, the reaction solution becoming pale. 60 parts of xylene were then added and the water of reaction was separated off in the course of 2 hours, using xylene as an entraining agent. Excess n-butanol was separated off by distillation, and a virtually colorless product remained. Iodine color number: 1 (according to DIN 6162).

EXAMPLE 2 (Comparative example)

The procedure described in Example 1 was followed, except that the perborate was omitted. After the water of reaction had been separated off, a brown oil was obtained. When 7.4 parts of sodium perborate tetrahydrate or an equivalent amount of $H_2O_2$ were added and the excess nbutanol was separated off by distillation, the oil could only be lightened to a medium yellow color. Iodine color number: 10–15 (DIN 6162).

EXAMPLE 3

The procedure described in Example 1 was followed, except that 6.6 parts of Na metaborate tetrahydrate were added instead of Na perborate. Iodine color number: 5–7 (DIN 6162).

EXAMPLE 4

The procedure described in Example 1 was followed, except that 9.2 parts of borax (disodium tetraborate decahydrate) were added instead of Na perborate. Iodine color number: 5–7 (DIN 6162).

We claim:

1. A process for the preparation of an alkylglucoside by acetalization of glucose in the anhydrous form with a $C_3$–$C_5$-alkanol in the presence of an acidic catalyst, wherein the acetalization is carried out with 1.5 to 5 parts of alcohol per part of anhydrous glucose and with an acidic catalyst selected from the group consisting of sulfuric acid, phosphoric acid, hydrochloric acid and p-toluenesulfonic acid, used in an amount of about 0.2–5% by weight, based on glucose, and in the presence of an alkali metal salt selected from the group consisting of sodium metalborate, borax and sodium perborate, used in an amount which is equivalent to or in excess of the amount of the acidic catalyst.

2. A process as claimed in claim 1, wherein the alkali metal salt selected from the group consisting of sodium metaborate, borax and sodium perborate is added to the solution obtained after the alkanol, glucose and acidic catalyst have been heated, and the reaction is then completed, the water of reaction formed being separated off by distillation.

3. A process is claimed in claim 1, wherein glucose in the anhydrous form is reacted with n-butanol.

* * * * *